United States Patent [19]
Rizoiu et al.

[11] Patent Number: 5,785,521
[45] Date of Patent: Jul. 28, 1998

[54] FLUID CONDITIONING SYSTEM

[75] Inventors: Ioana M. Rizoiu, Capistrano Beach; Andrew L. Kimmel, San Clemente, both of Calif.

[73] Assignee: BioLase Technology, Inc., San Clemente, Calif.

[21] Appl. No.: 575,775

[22] Filed: Dec. 20, 1995

Related U.S. Application Data

[63] Continuation-in-part of Ser. No. 522,503, Aug. 31, 1995.

[51] Int. Cl.[6] .................................................. A61C 3/02
[52] U.S. Cl. .............................. 433/29; 433/82; 433/86; 433/104
[58] Field of Search ........................ 433/101, 80, 81, 433/82, 84, 85, 86, 87, 104, 29; 606/3, 33, 10, 13; 219/121.84

[56] References Cited

U.S. PATENT DOCUMENTS

| | | | |
|---|---|---|---|
| 3,679,863 | 7/1972 | Houldcroft et al. | 219/121 LM |
| 3,924,335 | 12/1975 | Balamuth et al. | 433/119 |
| 3,991,296 | 11/1976 | Kojima et al. | 219/121 L |
| 4,193,197 | 3/1980 | Kuris et al. | 433/82 |
| 4,315,742 | 2/1982 | Nash et al. | 433/86 |
| 4,724,299 | 2/1988 | Hemmeke | 219/121 L |
| 4,741,697 | 5/1988 | Herbison | 433/80 |
| 4,826,431 | 5/1989 | Fujimura et al. | 433/29 |
| 4,961,923 | 10/1990 | Heyde | 433/86 |
| 4,973,247 | 11/1990 | Varnes et al. | 433/85 |
| 4,990,087 | 2/1991 | De Rocchis et al. | 433/104 |
| 5,092,864 | 3/1992 | Hayes et al. | 606/10 |
| 5,151,029 | 9/1992 | Levy | 433/29 |
| 5,199,870 | 4/1993 | Steiner et al. | 433/29 |
| 5,267,856 | 12/1993 | Wolbarsht et al. | 433/29 |
| 5,275,558 | 1/1994 | Seney | 433/82 |
| 5,318,562 | 6/1994 | Levy et al. | 606/16 |
| 5,334,019 | 8/1994 | Goldsmith et al. | 433/88 |
| 5,388,988 | 2/1995 | Goisser et al. | 433/29 |
| 5,401,171 | 3/1995 | Paghdiwala | 433/215 |
| 5,409,376 | 4/1995 | Murphy | 433/29 |
| 5,419,703 | 5/1995 | Warrin et al. | 433/86 |
| 5,474,451 | 12/1995 | Dalrymple et al. | 433/80 |

FOREIGN PATENT DOCUMENTS

| | | | |
|---|---|---|---|
| 0181199 | 5/1986 | European Pat. Off. | |
| 0454312 | 10/1991 | European Pat. Off. | |
| 4138468 | 3/1993 | Germany. | |
| 5945092 | 3/1984 | Japan. | |
| 2270846 | 3/1994 | United Kingdom | 433/82 |

OTHER PUBLICATIONS

New Laser—Matter Interaction Concept to Enhance Hard Tissue Cutting Efficiency by Ioana M. Rizoiu and Larry G. DeShazer, published in SPIE vol. 2134A Laser-Tissue Interaction V(1994)/309.

*Primary Examiner*—Cary E. O'Connor
*Attorney, Agent, or Firm*—Kenton R. Mullins

[57] ABSTRACT

A fluid conditioning system is adaptable to condition the water or air used in medical and dental cutting, irrigating, evacuating, cleaning, and drilling operations. The air or water may be conditioned by adding flavor, scent, saline, medications, and disinfectants. In addition to the direct benefits obtained from introduction of these agents, the laser cutting properties may be varied from the selective introduction of the various agents.

38 Claims, 6 Drawing Sheets

5,785,521

1

FLUID CONDITIONING SYSTEM

This application is a continuation-in-part of U.S. application Ser. No. 05/522,503 filed on Aug. 31, 1995, pending, and entitled USER PROGRAMMABLE COMBINATION OF ATOMIZED PARTICLES FOR ELECTROMAGNETICALLY INDUCED CUTTING, which is commonly assigned and the contents of which are expressly incorporated herein by reference.

BACKGROUND OF THE INVENTION

The present invention relates generally to medical cutting, irrigating, evacuating, cleaning, and drilling techniques and, more particularly to a system for introducing conditioned fluids into the cutting, irrigating, evacuating, cleaning, and drilling techniques.

A prior art dental/medical work station 11 is shown in FIG. 1. A vacuum line 12 and an air supply line 13 supply negative and positive pressures, respectively. A water supply line 14 and an electrical outlet 15 supply water and power, respectively. The vacuum line 12, the air supply line 13, the water supply line 14, and the power source 15 are all connected to the dental/medical unit 16.

The dental/medical unit 16 may comprise a dental seat or an operating table, a sink, an overhead light, and other conventional equipment used in dental and medical procedures. The dental/medical unit 16 provides water, air, vacuum and/or power to the instruments 17. These instruments may include an electrocauterizer, an electromagnetic energy source, a mechanical drill, a mechanical saw, a canal finder, a syringe, and/or an evacuator.

The electromagnetic energy source is typically a laser coupled with a delivery system. The laser 18a and delivery system 19a, both shown in phantom, as well as any of the above-mentioned instruments, may be connected directly to the dental/medical unit 16. Alternatively, the laser 18b and delivery system 19b, both shown in phantom, may be connected directly to the water supply 14, the air supply 13, and the electric outlet 15. Other instruments 17 may be connected directly to any of the vacuum line 12, the air supply line 13, the water supply line 14, and/or the electrical outlet 15.

The laser 18 and delivery system 19 may typically comprise an electromagnetic cutter for dental use. A conventional prior art electromagnetic cutter is shown in FIG. 2. According to this prior art apparatus, a fiber guide tube 30, a water line 31, an air line 32, and an air knife line 33 (which supplies pressurized air) may be fed from the dental/medical unit 16 into the hand-held apparatus 34. A cap 35 fits onto the hand-held apparatus 34 and is secured via threads 36. The fiber guide tube 30 abuts within a cylindrical metal piece 37. Another cylindrical metal piece 38 is a part of the cap 35. When the cap 35 is threaded onto the hand-held device 34, the two cylindrical metal tubes 37 and 38 are moved into very close proximity of one another. The pressurized air from the air knife line 33 surrounds and cools the laser as the laser bridges the gap between the two metal cylindrical objects 37 and 38. Air from the air knife line 33 flows out of the two exhausts 39 and 41 after cooling the interface between elements 37 and 38.

The laser energy exits from the fiber guide tube 42 and is applied to a target surface within the patient's mouth, according to a predetermined surgical plan. Water from the water line 31 and pressurized air from the air line 32 are forced into the mixing chamber 43. The air and water mixture is very turbulent in the mixing chamber 43, and

2 exits this chamber through a mesh screen with small holes 44. The air and water mixture travels along the outside of the fiber guide tube 42, and then leaves the tube 42 and contacts the area of surgery. The air and water spray coming from the tip of the fiber guide tube 42 helps to cool the target surface being cut and to remove materials cut by the laser.

Water is generally used in a variety of laser cutting operations in order to cool the target surface. Additionally, water is used in mechanical drilling operations for cooling the target surface and removing cut or drilled materials therefrom. Many prior art cutting or drilling systems use a combination of air and water, commonly combined to form a light mist, for cooling a target surface and/or removing cut materials from the target surface.

The use of water in these prior art systems has been somewhat successful for the limited purposes of cooling a target surface or removing debris therefrom. These prior art uses of water in cutting and drilling operations, however, have not allowed for versatility, outside of the two functions of cooling and removing debris. In particular, during cutting or drilling operations, medication treatments, preventative measure applications, and aesthetically pleasing substances, such as flavors or aromas, have not been possible or used. A conventional drilling operation may benefit from the use of an anesthetic near the drilling operation, for example, but during this drilling operation only water and/or air has so far been used. In the case of a laser cutting operation, a disinfectant, such as iodine, could be applied to the target surface during drilling to guard against infection, but this additional disinfectant has not been applied during such laser cutting operations. In the case of an oral drilling or cutting operation, unpleasant tastes or odors may be generated, which may be unpleasing to the patient. The conventional use of only water during this oral procedure does not mask the undesirable taste or odor. A need has thus existed in the prior art for versatility of applications and of treatments during drilling and cutting procedures.

Compressed gases, pressurized air, and electrical motors are commonly used to provide the driving force for mechanical cutting instruments, such as drills, in dentistry and medicine. The compressed gases and pressurized water are subsequently ejected into the atmosphere in close proximity to or inside of the patient's mouth and/or nose. The same holds true for electrically driven turbines when a cooling spray (air and water) is typically ejected into the patient's mouth, as well. These ejected fluids commonly contain vaporous elements of burnt flesh or drilled tissue structure. This odor can be quite uncomfortable for the patient, and can increase trauma experienced by the patient during the drilling or cutting procedure. In a such a drilling or cutting procedure, a mechanism for masking the smell and the odor generated from the cutting or drilling may be advantageous.

Another problem exists in the prior art with bacteria growth on surfaces within a dental operating room. The interior surfaces of air, vacuum, and water lines of the dental unit, for example, are subject to bacteria growth. Additionally, the air and water used to cool the tissue being cut or drilled within the patient's mouth is often vaporized into the air to some degree. This vaporized air and water condensates on surfaces of the dental equipment within the dental operating room. These moist surfaces can also promote bacteria growth, which is undesirable. A system for reducing the bacteria growth within air, vacuum, and water lines, and for reducing the bacteria growth resulting from condensation on exterior surfaces, is needed to reduce sources of contamination within a dental operating room.

SUMMARY OF THE INVENTION

The fluid conditioning system of the present invention is adaptable to most existing medical and dental cutting, irrigating, evacuating, cleaning, and drilling apparatuses. Flavored fluid is used in place of regular tap water during drilling operations. In the case of a laser surgical operation, electromagnetic energy is focused in a direction of the tissue to be cut, and a fluid router routes flavored fluid in the same direction. The flavored fluid may appeal to the taste buds of the patient undergoing the surgical procedure, and may include any of a variety of flavors, such as a fruit flavor or a mint flavor. In the case of a mist or air spray, scented air may be used to mask the smell of burnt or drilled tissue. The scent may function as an air freshener, even for operations outside of dental applications.

The fluids used for cooling a surgical site and/or removing tissue may further include an ionized solution, such as a biocompatible saline solution, and may further include fluids having predetermined densities, specific gravities, pH levels, viscosities, or temperatures, relative to conventional tap water. Additionally, the fluids may include a medication, such as an antibiotic, a steroid, an anesthetic, an anti-inflammatory, an antiseptic or disinfectant, adrenaline, epinephrine, or an astringent. The fluid may also include vitamins, herbs, or minerals.

Introduction of any of the above-mentioned conditioning agents to the conventional water of a cutting or drilling operation may be controlled by a user input. Thus, for example, a user may adjust a knob or apply pressure to a foot pedal in order to introduce iodine into the water after a cutting operation has been performed. The amount of conditioning applied to the air, water, or mist may be a function of the position of the foot pedal, for example.

According to one broad aspect of the present invention, a mist of atomized particles is placed into a volume of air above the tissue to be cut, and a source of electromagnetic energy, such as a laser, is focused into the volume of air. The electromagnetic energy has a wavelength, which is substantially absorbed by the atomized particles in the volume air. This absorption of the electromagnetic energy by the atomized particles causes the atomized particles to explode and impart mechanical cutting forces onto the tissue. According to this feature, the electromagnetic energy source does not directly cut the tissue but, rather, the exploded fluid particles are used to cut the tissue. These fluid particles may be conditioned with flavors, scents, ionization, medications, disinfectants, and other agents, as previously mentioned.

Since the electromagnetic energy is focused directly on the atomized, conditioned fluid particles, the cutting forces are changed, depending upon the conditioning of the atomized fluid particles. The mechanical cutting efficiency is proportional (related) to the absorption of the electromagnetic energy by the fluid spray. The absorption characteristic can be modified by changing the fluid composition. For example, introduction of a salt into the water before atomization, resulting in an ionized solution, will exhibit slower cutting properties than does regular water. This slower cutting may be desirable, or the laser power may be increased to compensate for the ionized, atomized fluid particles. Additionally, the atomized fluid particles may be pigmented to either enhance or retard absorption of the electromagnetic energy, to thereby additionally control the cutting power of the system. Two sources of fluid may be used, with one of the sources having a pigment and the other not having a pigment.

Another feature of the present invention places a disinfectant in the air, mist, or water used for dental applications. This disinfectant can be periodically routed through the air, mist, or water lines to disinfect the interior surfaces of these lines. This routing of disinfectant can be performed between patients, daily, or at any other predetermined intervals. A mouthwash may be used, for example, at the end of each procedure to both clean the patient's mouth and clean the air and water tubes.

According to another feature of the present invention, when disinfectant is routed through the lines during a medical procedure, the disinfectant stays with the water or mist, as the water or mist becomes airborne and settles on surrounding surfaces within the dental operating room. Bacteria growth within the lines, and from the condensation, is significantly attenuated, since the disinfectant retards bacteria growth on the moist surfaces.

The present invention, together with additional features and advantages thereof, may best be understood by reference to the following description taken in connection with the accompanying illustrative drawings.

DETAILED DESCRIPTION OF THE PREFERRED EMBODIMENTS

Figure 1:
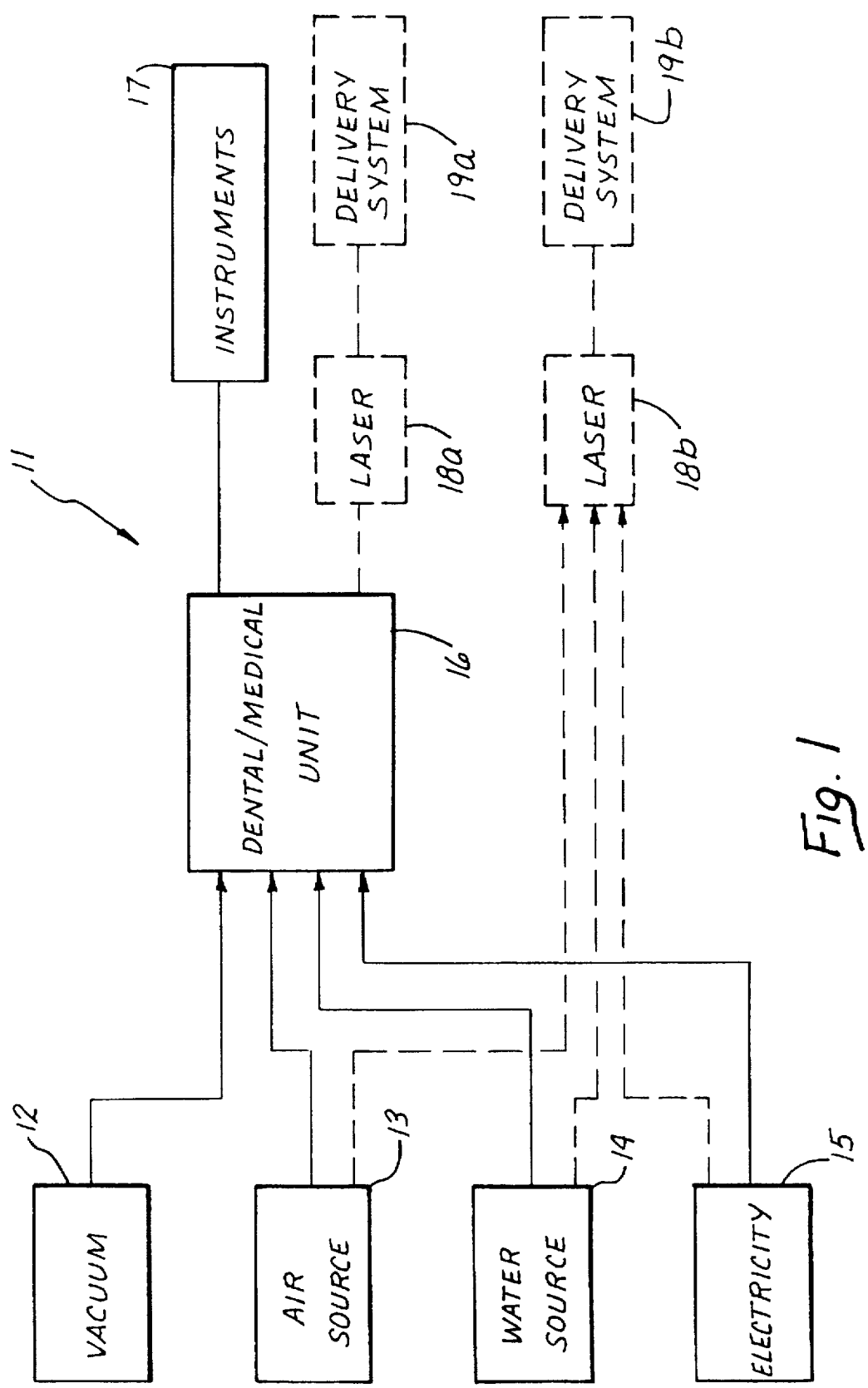
FIG. 1 illustrates a conventional dental/medical work station.
Figure 3:
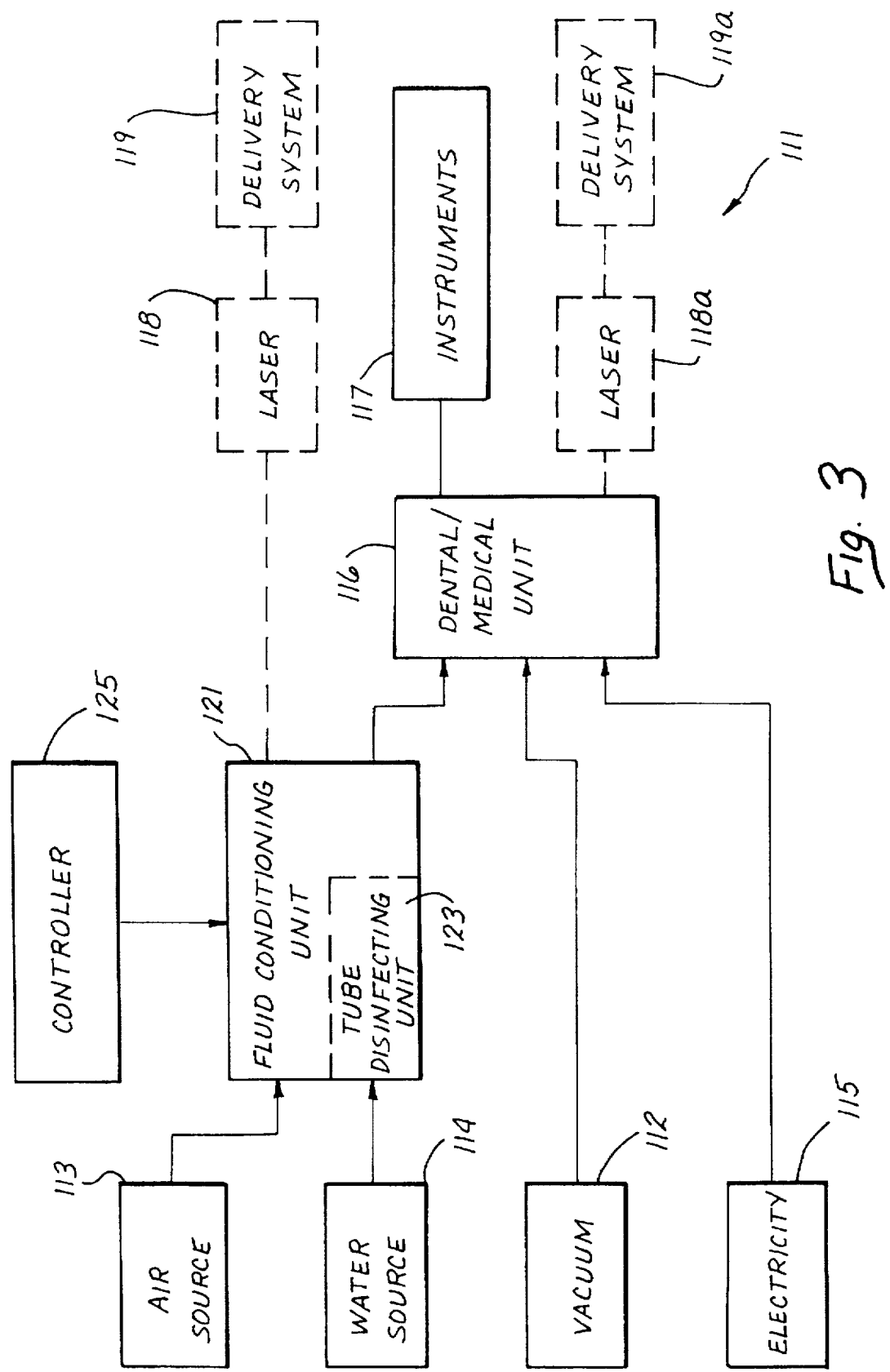
FIG. 3 illustrates a dental/medical work station according to the present invention.

The dental/medical work station 111 of the present invention is shown in FIG. 3, with elements similar to those shown in FIG. 1 proceeded by a "1". The dental/medical work station 111 comprises a conventional air line 113 and a conventional water line 114 for supplying air and water, respectively. A vacuum line 112 and an electrical outlet 115 supply negative air pressure and electricity to the dental/medical unit 116, similarly to the vacuum 12 and electrical 15 lines shown in FIG. 1. The fluid conditioning unit 121 may, alternatively, be placed between the dental/medical unit 116 and the instruments 117, for example. According to the present invention, the air line 113 and the water line 114 are both connected to a fluid conditioning unit 121.

A controller 125 allows for user inputs, to control whether air from the air line 113, water from the water line 114, or both, are conditioned by the fluid conditioning unit 121. A variety of agents may be applied to the air or water by the fluid conditioning unit 121, according to a configuration of the controller 125, for example, to thereby condition the air or water, before the air or water is output to the dental/medical unit 116. Flavoring agents and related substances, for example, may be used, such as disclosed in 21 C.F.R. Sections 172.510 and 172.515, the details of which are incorporated herein by reference. Colors, for example, may also be used for conditioning, such as disclosed in 21 C.F.R. Section 73.1 to Section 73.3126.

Similarly to the instruments 17 shown in FIG. 1, the instruments 117 may comprise an electrocauterizer, an electromagnetic energy source, a laser, a mechanical drill, a mechanical saw, a canal finder, a syringe, and/or an evacuator. All of these instruments 117 use air from the air line 113 and/or water from the water line 114, which may or may not be conditioned depending on the configuration of the controller 125. Any of the instruments 117 may alternatively be connected directly to the fluid conditioning unit 121 or directly to any of the air 113, water 114, vacuum 112, and/or electric 115 lines. For example, a laser 118 and delivery system 119 is shown in phantom connected to the fluid conditioning unit 121. The laser 118a and delivery system 119a may be connected to the dental/medical unit 116, instead of being grouped with the instruments 117.

Figure 4:
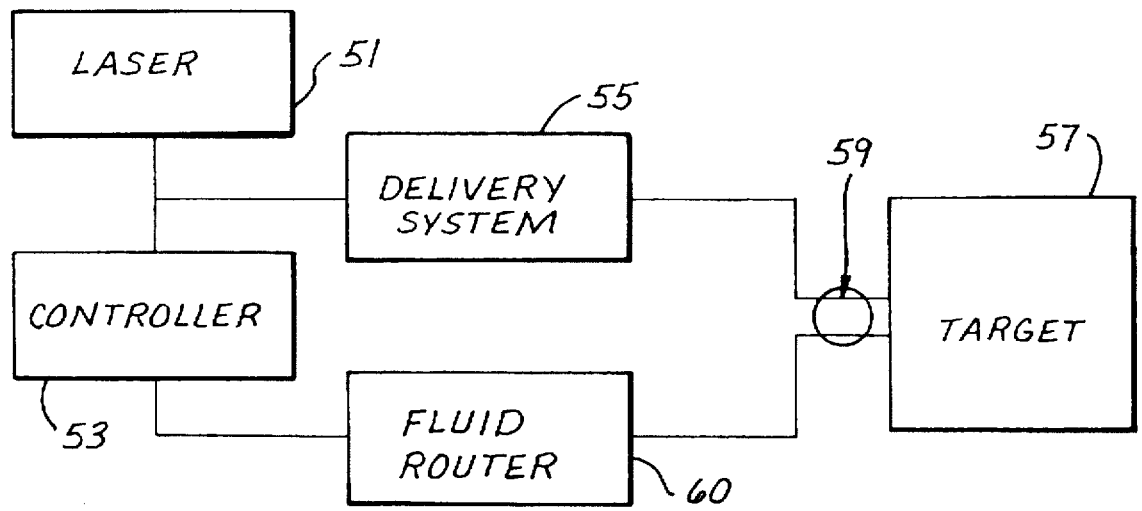
FIG. 4 is a schematic block diagram illustrating an electromagnetic cutter using conditioned fluid, according to one embodiment of the present invention.

The block diagram shown in FIG. 4 illustrates one embodiment of a laser 51 directly coupled with, for example, the air 113, water 114, and power 115 lines of FIG. 3. A separate fluid conditioning system is used in this embodiment. As an alternative to the laser, or any other tool being connected directly to any or all of the four supply lines 113–115 and having an independent fluid conditioning unit, any of these tools may instead, or additionally, be connected to the dental/medical unit 116 or the fluid conditioning unit 121, or both.

According to the exemplary embodiment shown in FIG. 4, an electromagnetically induced mechanical cutter is used for cutting. Details of this cutter are disclosed in co-pending U.S. patent application, Ser. No. 08/522,503, assigned to the assignee of this application. The electromagnetic cutter energy source 51 is connected directly to the outlet 115 (FIG. 3), and is coupled to both a controller 53 and a delivery system 55. The delivery system 55 routes and focuses the laser 51. In the case of a conventional laser system, thermal cutting forces are imparted onto the target 57. The delivery system 55 preferably comprises a fiberoptic guide for routing the laser 51 into an interaction zone 59, located above the target surface 57. The fluid router 60 preferably comprises an atomizer for delivering user-specified combinations of atomized fluid particles into the interaction zone 59. The atomized fluid particles are conditioned, according to the present invention, and may comprise flavors, scents, saline, and other agents, as discussed below.

In the case of a conventional laser, a stream or mist of conditioned fluid is supplied by the fluid router 60. The controller 53 may control various operating parameters of the laser 51, the conditioning of the fluid from the fluid router 60, and the specific characteristics of the fluid from the fluid router 60.

Figure 5A:
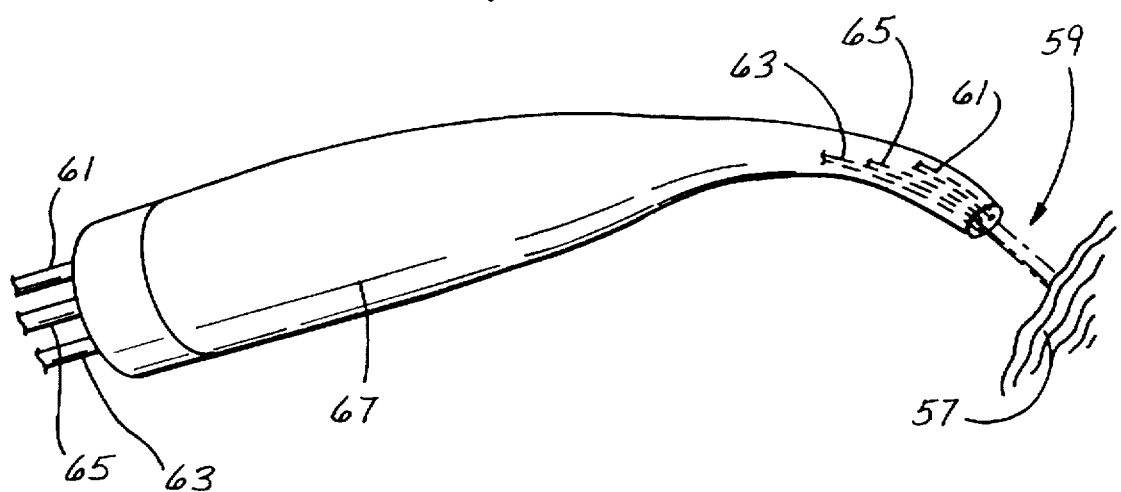
FIG. 5a illustrates one embodiment of the electromagnetic cutter of FIG. 2.

Although the present invention may be used with conventional drills and lasers, for example, one preferred embodiment is the electromagnetically induced mechanical cutter. Other preferred embodiments include an electrocauterizer, a syringe, an evacuator, or any air or electrical driver, drilling, filling, or cleaning mechanical instrument. FIG. 5a shows a simple embodiment of the electromagnetically induced mechanical cutter, in which a fiberoptic guide 61, an air tube 63, and a fluid tube 65 are placed within a hand-held housing 67. Although a variety of connections are possible, the air tube 63 and water tube 65 are preferably connected to either the fluid conditioning unit 121 or the dental/medical unit 116 of FIG. 3. The fluid tube 65 is preferably operated under a relatively low pressure, and the air tube 63 is preferably operated under a relatively high pressure.

According to the present invention, either the air from the air tube 63 or the fluid from the fluid tube 65, or both, are selectively conditioned by the fluid conditioning unit 121, as controlled by the controller 125. The laser energy from the fiberoptic guide 61 focuses onto a combination of air and fluid, from the air tube 63 and the fluid tube 65, at the interaction zone 59. Atomized fluid particles in the air and fluid mixture absorb energy from the laser energy of the fiberoptic tube 61, and explode. The explosive forces from these atomized fluid particles impart mechanical cutting forces onto the target 57.

Turning back to FIG. 2, a conventional optical cutter focuses laser energy on a target surface at an area A, for example, and the electromagnetically induced mechanical cutter focuses laser energy into an interaction zone B, for example. The conventional optical cutter uses the laser energy directly to cut tissue, and the electromagnetically induced mechanical cutter uses the laser energy to expand atomized fluid particles to thus impart mechanical cutting forces onto the target surface. The atomized fluid particles are heated, expanded, and cooled before contacting the target surface.

Figure 5B:
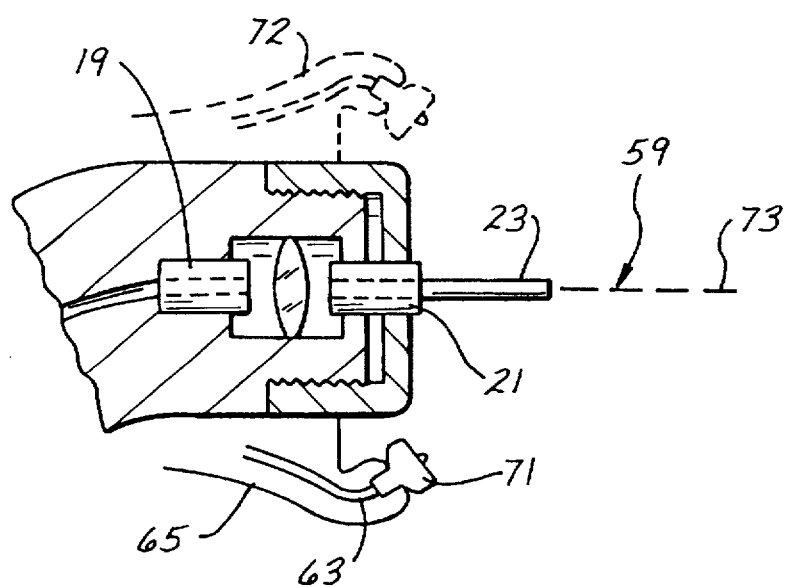
FIG. 5b illustrates another embodiment of the electromagnetic cutter of FIG. 2.

FIG. 5b illustrates a preferred embodiment of the electromagnetically induced mechanical cutter. The atomizer for generating atomized fluid particles comprises a nozzle 71, which may be interchanged with other nozzles (not shown) for obtaining various spatial distributions of the atomized fluid particles, according to the type of cut desired. A second nozzle 72, shown in phantom lines, may also be used. In a simple embodiment, a user controls the air and water pressure entering into the nozzle 71. The nozzle 71 is thus capable of generating many different user-specified combinations of atomized fluid particles and aerosolized sprays.

Intense energy is emitted from the fiberoptic guide 23. This intense energy is preferably generated from a coherent source, such as a laser. In the presently preferred embodiment, the laser comprises an erbium, chromium, yttrium, scandium, gallium garnet (Er, Cr:YSGG) solid state laser. When fluids besides mere water are used, the absorption of the light energy changes and cutting efficiency is thus affected. Alternatively, when using certain fluids containing pigments or dyes, laser systems of different wavelengths such as Neodymium yttrium aluminum garnet-Nd:YAG wavelengths may be selected to allow for high absorption by the fluid.

The delivery system 55 for delivering the electromagnetic energy includes a fiberoptic energy guide or equivalent which attaches to the laser system and travels to the desired work site. Fiberoptics or waveguides are typically long, thin and lightweight, and are easily manipulated. Fiberoptics can be made of calcium fluoride (CaF), calcium oxide (CaO2), zirconium oxide (ZrO2), zirconium fluoride (ZrF), sapphire, hollow waveguide, liquid core, TeX glass, quartz silica, germanium sulfide, arsenic sulfide, germanium oxide (GeO2), and other materials. Other delivery systems include devices comprising mirrors, lenses and other optical components where the energy travels through a cavity, is directed by various mirrors, and is focused onto the targeted cutting site with specific lenses.

The preferred embodiment of light delivery for medical applications of the present invention is through a fiberoptic conductor, because of its light weight, lower cost, and ability to be packaged inside of a handpiece of familiar size and weight to the surgeon, dentist, or clinician. Non-fiberoptic systems may be used in both industrial applications and medical applications, as well. The nozzle 71 is employed to create an engineered combination of small particles of the chosen fluid. The nozzle 71 may comprise several different designs including liquid only, air blast, air assist, swirl, solid cone, etc. When fluid exits the nozzle 71 at a given pressure and rate, it is transformed into particles of user-controllable sizes, velocities, and spatial distributions.

Figure 6A:
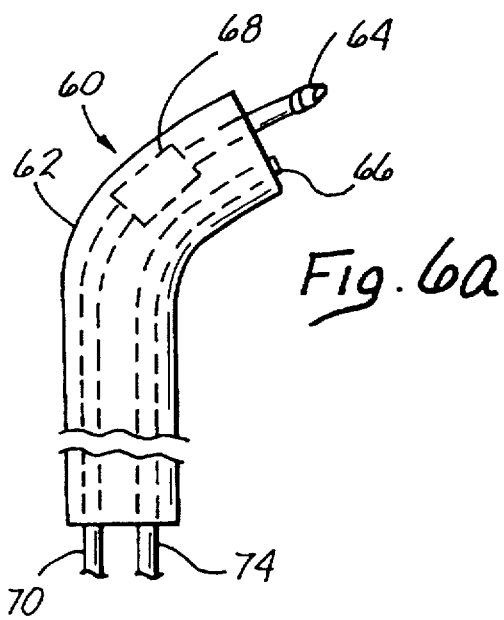
FIG. 6a illustrates a mechanical drilling apparatus according to the present invention.

A mechanical drill 60 is shown in FIG. 6a, comprising a handle 62, a drill bit 64, and a water output 66. The mechanical drill 60 comprises a motor 68, which may be electrically driven, or driven by pressurized air.

When the motor 68 is driven by air, for example, the fluid enters the mechanical drill 60 through the first supply line 70. Fluid entering through the first supply line 70 passes through the motor 68, which may comprise a turbine, for example, to thereby provide rotational forces to the drill bit 64. A portion of the fluid, which may not appeal to a patient's taste and/or smell, may exit around the drill bit 64, coming into contact with the patient's mouth and/or nose. The majority of the fluid exits back through the first supply line 70.

In the case of an electric motor, for example, the first supply line 70 provides electric power. The second supply line 74 supplies fluid to the fluid output 66. The water and/or air supplied to the mechanical drill 60 may be selectively conditioned by the fluid conditioning unit 121, according to the configuration of the controller 125.

Figure 6B:
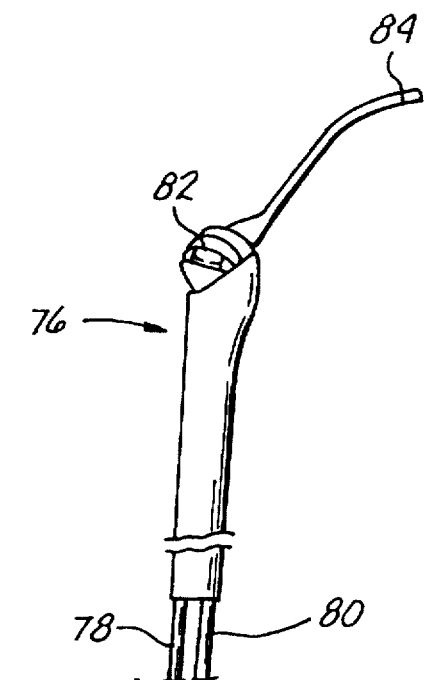
FIG. 6b illustrates a syringe according to the present invention.

The syringe 76 shown in FIG. 6b comprises an air input line 78 and a water input line 80. A user control 82 is movable between a first position and a second position. The first position supplies air from the air line 78 to the output tip 84, and the second position supplies water from the water line 80 to the output tip 84. Either the air from the air line 78, the water from the water line 80, or both, may be selectively conditioned by the fluid conditioning unit 121, according to the configuration of the controller 125, for example.

Figures 2, 7:
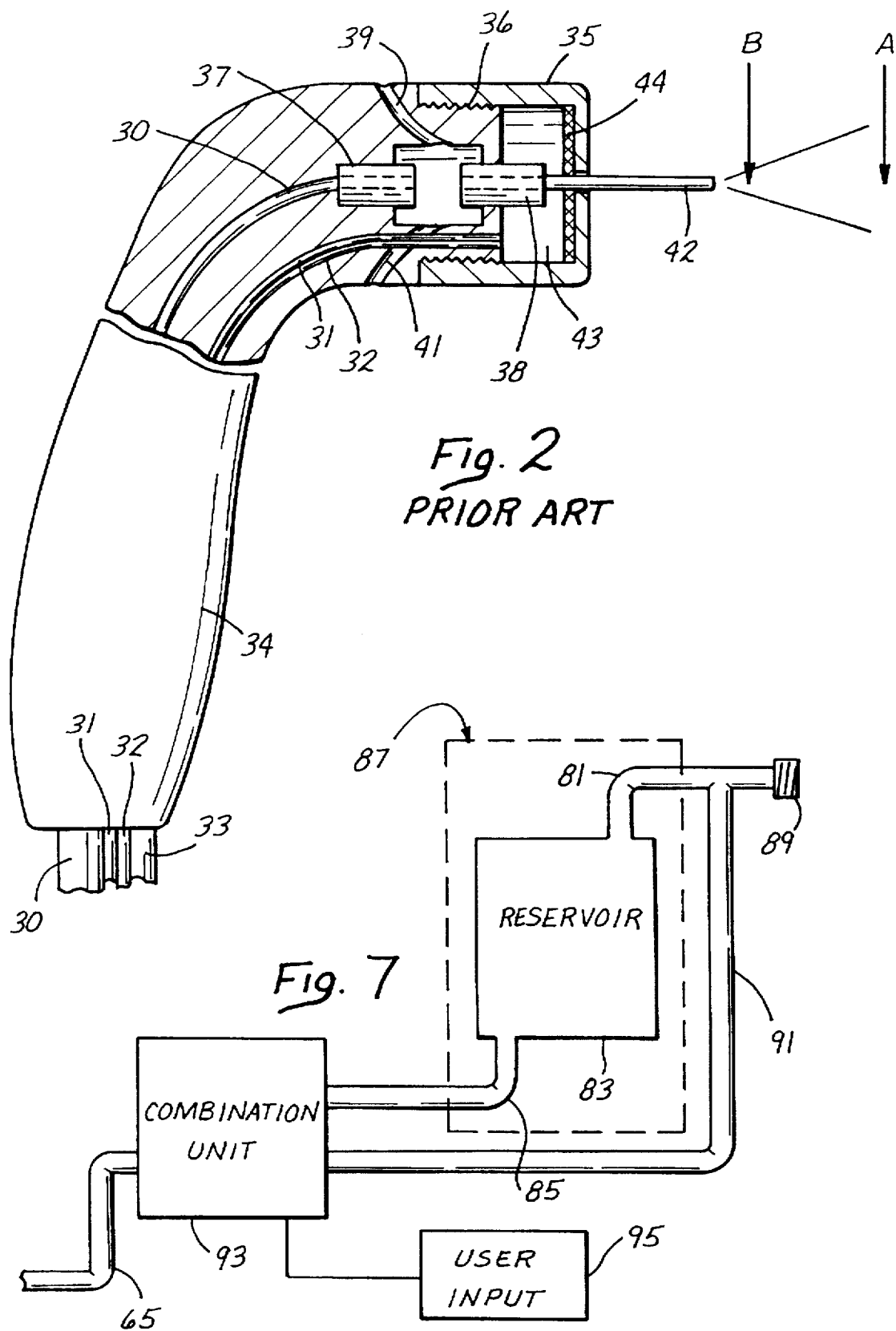
FIG. 2 is a conventional optical cutter apparatus.
FIG. 7 illustrates the fluid conditioning system of the present invention.

Turning to FIG. 7, a portion of the fluid conditioning unit 121 (FIG. 3) is shown. This fluid conditioning unit 121 is preferably adaptable to existing water lines 114, for providing conditioned fluid to the dental/medical unit 116 as a substitute for regular tap water in drilling and cutting operations, for example. The interface 89 connects to an existing water line 114 and feeds water through the fluid-in line 81 and the bypass line 91. The reservoir 83 accepts water from the fluid-in line 81 and outputs conditioned fluid to the fluid-out line 85. The fluid-in line 81, the reservoir 83, and the fluid-out line 85 together comprise a fluid conditioning subunit 87.

Conditioned fluid is output from the fluid conditioning subunit 87 into the combination unit 93. The fluid may be conditioned by conventional means, such as the addition of a tablet, liquid syrup, or a flavor cartridge. Also input into the combination unit 93 is regular water from the bypass line 91. A user input 95 into the controller 125, for example, determines whether fluid output from the combination unit 93 into the fluid tube 65 comprises only conditioned fluid from the fluid-out line 85, only regular water from the bypass line 91, or a combination thereof. The user input 95 comprises a rotatable knob, a pedal, or a foot switch, operable by a user, for determining the proportions of conditioned fluid and regular water. These proportions may be determined according to the pedal or knob position. In the pedal embodiment, for example, a full-down pedal position corresponds to only conditioned fluid from the fluid outline 85 being output into the fluid tube 65, and a full pedal up position corresponds to only water from the bypass line 91 being output into the fluid tube 65. The bypass line 91, the combination unit 93, and the user input 95 provide versatility, but may be omitted, according to preference. A simple embodiment for conditioning fluid would comprises only the fluid conditioning subunit 87.

Figure 8:
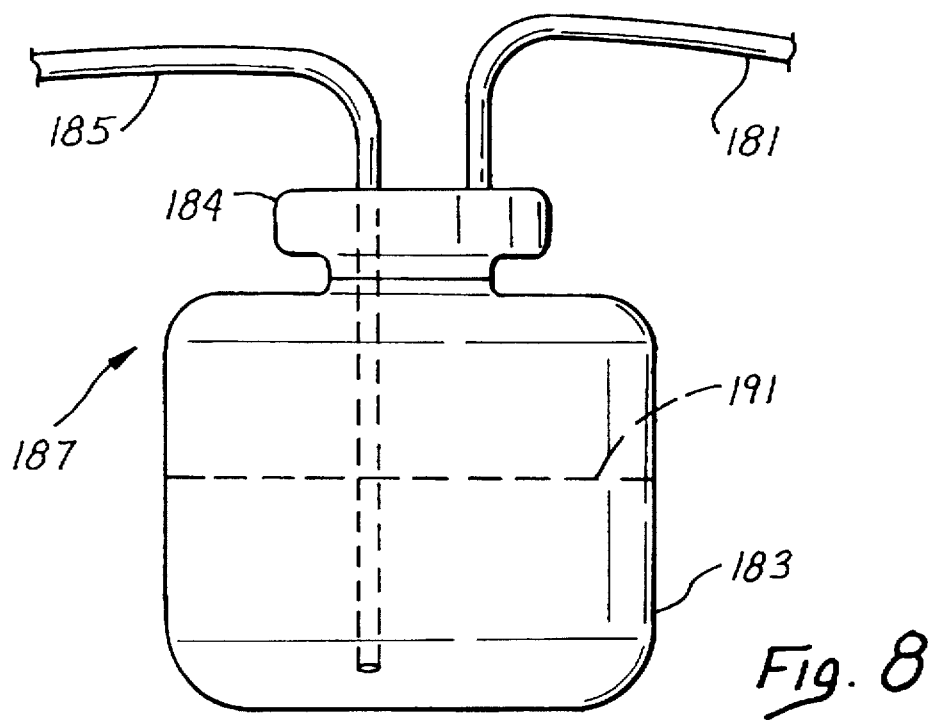
FIG. 8 illustrates one embodiment of the fluid conditioning unit of the present invention.

An alternative embodiment of the fluid conditioning subunit 87 is shown in FIG. 8. The fluid conditioning subunit 187 inputs air from air line 113 via an air input line 181, and outputs conditioned fluid via a fluid output line 185. The fluid output line 185 preferably extends vertically down into the reservoir 183 into the fluid 191 located therein. The lid 184 may be removed and conditioned fluid inserted into the reservoir 183. Alternatively, a solid or liquid form of fluid conditioner may be added to water already in the reservoir 183. The fluid is preferably conditioned, using either a scent fluid drop or a scent tablet (not shown), and may be supplied with fungible cartridges, for example.

Figure 9:
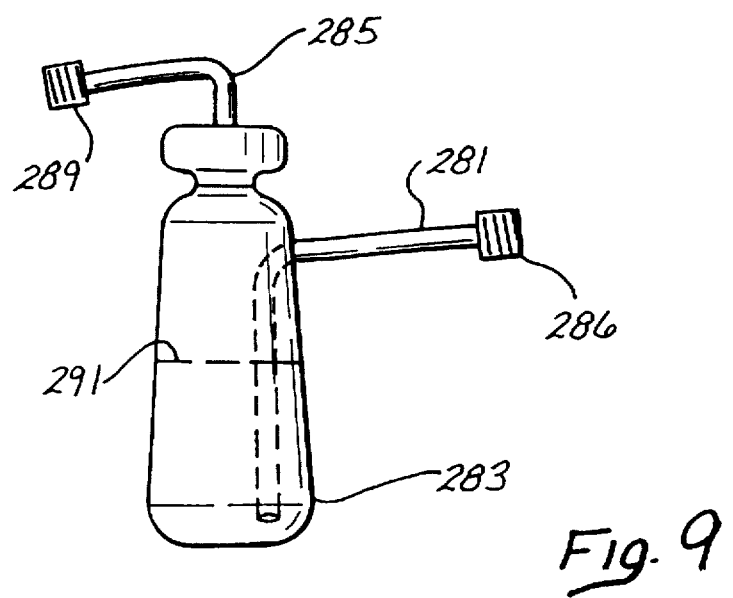
FIG. 9 illustrates the air conditioning unit of the present invention.

The fluid 191 within the reservoir 183 may be conditioned to achieve a desired flavor, such as a fruit flavor or a mint flavor, or may be conditioned to achieve a desired scent, such as an air freshening smell. A conditioned fluid having a scent, a scented mist, or a scented source of air, may be particularly advantageous for implementation in connection with an air conditioning unit, as shown in FIG. 9 and discussed below. In addition to flavor and scents, other conditioning agents may be selectively added to a conventional water line, mist line, or air line. For example, an ionized solution, such as saline water, or a pigmented solution may be added, as discussed below. Additionally, agents may be added to change the density, specific gravity, pH, temperature, or viscosity of water and/or air supplied to a drilling or cutting operation. Medications, such as antibiotics, steroids, anesthetics, anti-inflammatories, disinfectants, adrenaline, epinephrine, or astringents may be added to the water and/or air used in a drilling or cutting operation. For example, an astringent may be applied to a surgical area, via the water line to reduce bleeding. Vitamins, herbs, or minerals may also be used for conditioning the air or water used in a cutting or drilling procedure. An anesthetic or anti-inflammatory applied to a surgical wound may reduce discomfort to the patient or trauma to the wound, and an antibiotic or disinfectant may prevent infection to the wound.

The air conditioning subunit shown in FIG. 9 is connectible into an existing air line 113, via interfaces 286 and 289. Conventional air enters the conditioning subunit via the air input line 281, and exits an air output line 285. The air input line 281 preferably extends vertically into the reservoir 283 into a fluid 291 within the reservoir 283. The fluid 291 is preferably conditioned, using either a scent fluid drop or a scent tablet (not shown). The fluid 291 may be conditioned with other agents, as discussed above in the context of conditioning water. According to the present invention, water in the water line 31 or air in the air line 32 of a conventional laser cutting system (FIG. 2) is conditioned. Either the fluid tube 65 or the air tube 63 (FIG. 5a) of the electromagnetically induced mechanical cutter is conditioned. In addition to laser operations, the air and/or water of a dental drilling, irrigating, suction, or electrocautery system may also be conditioned.

Many of the above-discussed conditioning agents may change the absorption of the electromagnetic energy into the atomized fluid particles in the electromagnetically induced mechanical cutting environment of the presently preferred embodiment. Accordingly, the type of conditioning may effect the cutting power of an electromagnetic or an electromagnetically induced mechanical cutter. Thus, in addition to the direct benefits achievable through these various conditioning agents discussed above, such as flavor or medication, these various conditioning agents further provide versatility and programmability to the type of cut resulting from the electromagnetic or electromagnetically induced mechanical cutter. For example, introduction of a saline solution will reduce the speed of cutting. Such a biocompatible saline solution may be used for delicate cutting operations or, alternatively, may be used with a higher laser-power setting to approximate the cutting power achievable with regular water.

Pigmented fluids may also be used with the electromagnetic or the electromagnetically induced mechanical cutter, according to the present invention. The electromagnetic energy source may be set for maximum absorption of atomized fluid particles having a certain pigmentation, for example. These pigmented atomized fluid particles may then be used to achieve the mechanical cutting. A second water or mist source may be used in the cutting operation, but since this second water or mist is not pigmented, the interaction with the electromagnetic energy source is minimized. As just one example of many, this secondary mist or water source could be flavored.

According to another configuration, the atomized fluid particles may be unpigmented, and the electromagnetic or the electromagnetically induced energy source may be set to provide maximum energy absorption for these unpigmented atomized fluid particles. A secondary pigmented fluid or mist may then be introduced into the surgical area, and this secondary mist or water would not interact significantly with the electromagnetic energy source. As another example, a single source of atomized fluid particles may be switchable between pigmentation and non-pigmentation, and the electromagnetic energy source may be set to be absorbed by one of the two pigment states to thereby provide a dimension of controllability as to exactly when cutting is achieved.

Disinfectant may be added to an air or water source in order to combat bacteria growth within the air and water lines, and on surfaces within a dental operating room. The air and water lines of the dental unit 116, for example, may be periodically flushed with a disinfectant selected by the controller 125 and supplied by the fluid conditioning unit 121. An accessory tube disinfecting unit 123 may accommodate disinfecting cartridges and perform standardized or preprogrammed periodic flushing operations.

Even in a dental or medical procedure, an appropriate disinfectant may be used. The disinfectant may be applied at the end of a dental procedure as a mouthwash, for example, or may be applied during a medical or dental procedure. The air and water used to cool the tissue being cut or drilled within the patient's mouth, for example, is often vaporized into the air to some degree. According to the present invention, a conditioned disinfectant solution will also be vaporized with air or water, and condensate onto surfaces of the dental equipment within the dental operating room. Any bacteria growth on these moist surfaces is significantly attenuated, as a result of the disinfectant on the surfaces.

Although exemplary embodiments of the invention have been shown and described, many other changes, modifications and substitutions, in addition to those set forth in the above paragraph, may be made by one having ordinary skill in the art without necessarily departing from the spirit and scope of this invention.

We claim:

1. An apparatus for implementing a medical procedure, comprising:

a medical instrument comprising an electromagnetic energy source, the medical instrument being adapted to perform a medical-treatment function on an operating site located inside of or connected to a human body;

a fluid router for routing atomized flavored fluid particles in a direction of the operating site;

wherein the fluid router routes the atomized flavored fluid particles into a volume of air above the operating site; and wherein the electromagnetic energy source focuses electromagnetic energy into the volume of air, the electromagnetic energy having a wavelength which is substantially absorbed by the atomized flavored fluid particles in the volume of air, the absorption of the electromagnetic energy by the atomized flavored fluid particles causing the atomized flavored fluid particles to explode and impart disruptive mechanical forces onto the operating site.

2. The apparatus for implementing a medical procedure according to claim 1, further comprising means for switching between a first mode and a second mode, whereby the fluid router is operable between the first mode wherein the routed fluid is flavored, and the second mode wherein the routed fluid is not flavored.

3. An apparatus for implementing a medical procedure, comprising:

a medical instrument for performing a medical-treatment function on an operating site located inside of or connected to a human body;

a router comprising a scented substance and being adapted to route a scented medium in a direction of the operating site; and wherein the medical instrument comprises one of an electrocauterizer, an electromagnetic energy source for directing electromagnetic energy in a direction of the operating site, and a laser.

4. The apparatus for implementing a medical procedure according to claim 3, wherein the electromagnetic energy source focusses the electromagnetic energy on the operating site, wherein the scented medium comprises scented water, and wherein the router routes the scented water onto the operating site, to thereby cool the operating site as the operating site is being cut by the electromagnetic energy.

5. The apparatus for implementing a medical procedure according to claim 4, further comprising means for switching between a first mode and a second mode; wherein the router is operable between the first mode where the routed medium is scented, and the second mode where the routed medium is not scented.

6. The apparatus for implementing a medical procedure according to claim 3, wherein the electromagnetic energy source focusses the electromagnetic energy on the operating site, and wherein the scented medium comprises a scented mist, and wherein the router routes the scented mist onto the operating site, to thereby cool the operating site as the operating site is being cut by the electromagnetic energy.

7. The apparatus for implementing a medical procedure according to claim 3, wherein the router comprises an atomizer for atomizing the scented medium before routing the scented medium in the direction of the operating site.

8. An apparatus for implementing a medical procedure, comprising:

a medical instrument for performing a medical-treatment function on an operating site located inside of or connected to a human body;

a router comprising a scented substance and being adapted to route a scented medium in a direction of the operating site; and wherein the scented medium comprises scented air.

9. An apparatus for implementing a medical procedure, comprising:

a medical instrument for performing a medical-treatment function on an operating site located inside of or connected to a human body;

a router comprising a scented substance and being adapted to route a scented medium in a direction of the operating site;

wherein the medical instrument comprises one of an electrocauterizer, an electromagnetic energy source for directing electromagnetic energy in a direction of the operating site, and a laser;

wherein the router comprises an atomizer for atomizing the scented medium before routing the scented medium in the direction of the operating site;

wherein the atomizer routes the atomized scented medium into a volume of air above the operating site; and wherein the electromagnetic energy source focuses electromagnetic energy into the volume of air, the electromagnetic energy having a wavelength which is substantially absorbed by portions of the atomized scented medium in the volume of air, the absorption of the electromagnetic energy by the portions of the atomized scented medium causing the portions of the atomized scented medium to explode and impart disruptive mechanical forces onto the operating site.

10. The apparatus for implementing a medical procedure according to claim 9, further comprising means for switching between a first mode and a second mode; wherein the router is operable between the first mode where the routed medium is scented, and the second mode where the routed medium is not scented.

11. An apparatus for implementing a medical procedure, comprising:

a medical instrument for performing a medical-treatment function on an operating site located inside of or connected to a human body;

a fluid router comprising an ionizing substance and being adapted to route an ionized solution in a direction of the operating site;

wherein the medical instrument comprises one of an electrocauterizer, an electromagnetic energy source for directing electromagnetic energy in a direction of the operating site, and a laser;

wherein the fluid router comprises an atomizer for atomizing the ionized solution into atomized particles before routing the atomized particles in the direction of the operating site;

wherein the atomizer routes the atomized particles into a volume of air above the operating site, and wherein the electromagnetic energy source focuses electromagnetic energy into the volume of air, the electromagnetic energy having a wavelength which is substantially absorbed by the atomized particles in the volume of air, the absorption of the electromagnetic energy by the atomized particles causing the atomized particles to explode and impart disruptive mechanical forces onto the operating site.

12. An apparatus for implementing a medical procedure, comprising:

a medical instrument for performing a medical-treatment function on an operating site located inside of or connected to a human body;

a fluid router comprising an ionizing substance and being adapted to route an ionized solution in a direction of the operating site;

means for switching among a first mode, a second mode, and any of a plurality of modes between the first mode and the second mode;

wherein the medical instrument comprises one of an electrocauterizer, an electromagnetic energy source for directing electromagnetic energy in a direction of the operating site, and a laser;

whereby the fluid router is operable between the first mode wherein solution routed therefrom is ionized, and the second mode wherein solution routed therefrom is not ionized; and whereby the fluid router is operable in a plurality of modes between the first mode and the second mode to thereby continuously control a cutting power of the electromagnetic energy source.

13. The apparatus for implementing a medical procedure according to claim 12, wherein the cutting power of the electromagnetic energy source decreases as the fluid from the fluid router becomes more ionized.

14. The apparatus for implementing a medical procedure according to claim 13, wherein a strength of the electromagnetic energy source is adjustable to control the cutting power of the electromagnetic energy source.

15. The apparatus for implementing a medical procedure according to claim 14, wherein the strength of the electromagnetic energy source is adapted to be increased when the fluid from the fluid router becomes more ionized, to thereby maintain a constant cutting power of the electromagnetic energy source, and wherein the strength of the electromagnetic energy source is adapted to be decreased when the fluid from the fluid router becomes less ionized, to thereby maintain a constant cutting power of the electromagnetic energy source.

16. An apparatus for imparting mechanical forces onto a target surface, comprising:

an atomizer assembly comprising a pigmented substance and being adapted to place pigmented atomized fluid particles into a volume of air above the target surface; and an electromagnetic energy source for directing electromagnetic energy into the volume of air, the electromagnetic energy having a wavelength which is substantially absorbed by the pigmented atomized fluid particles in the volume of air, the absorption of the electromagnetic energy by the pigmented atomized fluid particles causing the pigmented atomized fluid particles to explode and impart disruptive mechanical forces onto the target surface.

17. An apparatus for imparting mechanical forces onto a target surface, comprising:

an atomizer for placing atomized fluid particles into a volume of air above the target surface;

an electromagnetic energy source for directing electromagnetic energy into the volume of air, the electromagnetic energy having a wavelength which is substantially absorbed by the atomized fluid particles in the volume of air, the absorption of the electromagnetic energy by the atomized fluid particles causing the atomized fluid particles to explode and impart disruptive mechanical forces onto the target surface; and a fluid source comprising a pigmented substance and being adapted to deliver pigmented fluid to an approximate vicinity of the target surface, the pigmented fluid having a color which is substantially unabsorbed by the electromagnetic energy.

18. An apparatus for imparting mechanical forces onto a target surface, comprising:

an atomizer for placing atomized fluid particles into a volume of air above the target surface;

an electromagnetic energy source for directing electromagnetic energy into the volume of air, the electromagnetic energy having a wavelength which is substantially absorbed by the atomized fluid particles in the volume of air, the absorption of the electromagnetic energy by the atomized fluid particles causing the atomized fluid particles to explode and impart disruptive mechanical forces onto the target surface; and supplying means connected to the atomizer, for selectively supplying a pigmentation to the atomized fluid particles.

19. The apparatus for imparting mechanical forces onto a target surface according to claim 18 wherein the pigmentation is selectively supplied to the atomized fluid particles according to a user input.

20. The apparatus for imparting mechanical forces onto a target surface according to claim 18, wherein the electromagnetic energy has a wavelength that is substantially absorbed by the atomized fluid particles when the pigmentation is supplied to the atomized fluid particles.

21. The apparatus for imparting mechanical forces onto a target surface according to claim 18, wherein the electromagnetic energy has a wavelength that is substantially absorbed by the atomized fluid particles when the pigmentation is not supplied to the atomized fluid particles.

22. The apparatus for imparting mechanical forces onto a target surface according to claim 18, wherein the atomizer comprises a water source line and an air source line, and wherein the pigmentation is selectively supplied to the atomized fluid particles via one of the air source line and the water source line.

23. An apparatus for implementing a medical procedure comprising:

a medical instrument for performing a medical-treatment function on an operating site located inside of or connected to a human body;

means for switching between a first mode and a second mode;

a router comprising a medication substance and being adapted to route a medication medium in a direction of the operating site, whereby the router is operable between the first mode wherein fluid routed therefrom is medicated, and the second mode wherein fluid routed therefrom is not medicated; and wherein the medication medium comprises one of a steroid, an anti-inflammatory, adrenaline, and epinephrine.

24. An apparatus for implementing a medical procedure comprising:

a medical instrument for performing a medical-treatment function on an operating site located inside of or connected to a human body;

means for switching between a first mode and a second mode;

a router comprising a medication substance and being adapted to route a medication medium in a direction of the operating site, whereby the router is operable between the first mode wherein fluid routed therefrom is medicated, and the second mode wherein fluid routed therefrom is not medicated; and wherein the medication medium comprises vitamins.

25. An apparatus for implementing a medical procedure comprising:

a medical instrument for performing a medical-treatment function on an operating site located inside of or connected to a human body;

means for switching between a first mode and a second mode;

a router comprising a medication substance and being adapted to route a medication medium in a direction of the operating site, whereby the router is operable between the first mode wherein fluid routed therefrom is medicated, and the second mode wherein fluid routed therefrom is not medicated; and wherein the medical instrument comprises one of an electrocauterizer, an electromagnetic energy source for directing electromagnetic energy in a direction of the operating site, and a laser.

26. The apparatus for implementing a medical procedure according to claim 25, wherein:

the medical instrument comprises an electromagnetic energy source;

the electromagnetic energy source focuses the electromagnetic energy on the operating site; and the router routes the medication medium onto the operating site to thereby cool and medicate the operating site as the operating site is being cut by the electromagnetic energy.

27. The apparatus for implementing a medical procedure according to claim 25, wherein the router comprises an atomizer for atomizing the medication medium into atomized particles before routing the medication medium in the direction of the operating site.

28. The apparatus for implementing a medical procedure according to claim 27, wherein the atomizer routes the atomized particles into a volume of air above the operating site, and wherein the electromagnetic energy source focuses electromagnetic energy into the volume of air, the electromagnetic energy having a wavelength which is substantially absorbed by the atomized particles in the volume of air, the absorption of the electromagnetic energy by the atomized particles causing the atomized particles to explode and impart disruptive mechanical forces onto the operating site.

29. An apparatus for implementing a medical procedure, comprising:

a medical instrument for performing a medical-treatment function on an operating site located inside of or connected to a human body;

receiving means for receiving an instruction from a user to supply a first type of fluid and for receiving an instruction from a user to supply a conditioned fluid;

a fluid router for selectively routing pigmented fluid in a direction of the tissue, the fluid router being adapted to route pigmented fluid upon receipt of an instruction into the receiving means to supply conditioned fluid; and wherein the medical instrument comprises one of an electrocauterizer, an electromagnetic energy source for directing electromagnetic energy in a direction of the operating site, and a laser.

30. The apparatus for implementing a medical procedure according to claim 29, further comprising means for switching between a first mode and a second mode; wherein the fluid router is operable between the first mode where the routed fluid is pigmented, and the second mode where the routed fluid is not pigmented.

31. The apparatus for implementing a medical procedure according to claim 30, wherein a wavelength of the electromagnetic energy source is substantially absorbed by the pigmented fluid.

32. An apparatus for imparting mechanical forces onto a target surface, comprising:

an atomizer assembly comprising a medicated substance and being adapted to place medicating atomized fluid particles into a volume of air above the target surface; and an electromagnetic energy source for directing electromagnetic energy into the volume of air, the electromagnetic energy having a wavelength which is substantially absorbed by the medicating atomized fluid particles in the volume of air, the absorption of the electromagnetic energy by the medicating atomized fluid particles causing the medicating atomized fluid particles to impart disruptive mechanical forces onto the target surface.

33. The apparatus for imparting mechanical forces onto a target surface according to claim 32, wherein the medicated substance comprises an anesthetic substance.

34. The apparatus for imparting mechanical forces onto a target surface according to claim 32, wherein the medicating atomized fluid particles comprise a sterile substance.

35. The apparatus for imparting mechanical forces onto a target surface according to claim 32, wherein the medicating atomized fluid particles comprise at least one of an antibiotic, iodine, a steroid, an anesthetic, an anti-inflammatory, a disinfectant, adrenaline, epinephrine, and a stringent.

36. An apparatus for imparting mechanical forces onto a target surface, comprising:

an atomizer assembly comprising a disinfectant substance and being adapted to place disinfecting atomized fluid particles into a volume of air above the target surface; and an electromagnetic energy source for directing electromagnetic energy into the volume of air, the electromagnetic energy having a wavelength which is substantially absorbed by the disinfecting atomized fluid particles in the volume of air, the absorption of the electromagnetic energy by the disinfecting atomized fluid particles causing the disinfecting atomized fluid particles to impart disruptive mechanical forces onto the target surface.

37. The apparatus for imparting mechanical forces onto a target surface according to claim 36, wherein the sterile substance comprises sterilized water.

38. The apparatus for imparting mechanical forces onto a target surface according to claim 36, wherein the disinfectant substance comprises a sterile substance.

* * * * *